(12) United States Patent
Kim et al.

(10) Patent No.: US 9,634,759 B2
(45) Date of Patent: Apr. 25, 2017

(54) SYSTEM AND APPARATUS FOR INSPECTING FIBER OPTIC CABLES

(71) Applicant: Fluke Corporation, Everett, WA (US)

(72) Inventors: Wonoh Kim, Johns Creek, GA (US); Randy Fischer, Flowery Branch, GA (US); J. David Schell, Austin, TX (US)

(73) Assignee: Fluke Corporation, Everett, WA (US)

( * ) Notice: Subject to any disclaimer, the term of this patent is extended or adjusted under 35 U.S.C. 154(b) by 32 days.

(21) Appl. No.: 14/107,898

(22) Filed: Dec. 16, 2013

(65) Prior Publication Data

US 2015/0171959 A1 Jun. 18, 2015

(51) Int. Cl.
| | | |
|---|---|---|
| *G01M 11/08* | (2006.01) | |
| *H04B 10/073* | (2013.01) | |
| *H04B 10/07* | (2013.01) | |
| *H04B 10/25* | (2013.01) | |
| *G01N 21/952* | (2006.01) | |
| *G02B 6/32* | (2006.01) | |
| *G02B 6/42* | (2006.01) | |

(52) U.S. Cl.
CPC ......... *H04B 10/073* (2013.01); *G01M 11/088* (2013.01); *H04B 10/07* (2013.01); *H04B 10/25* (2013.01); *G01N 21/952* (2013.01); *G02B 6/32* (2013.01); *G02B 6/4226* (2013.01); *G02B 6/4292* (2013.01)

(58) Field of Classification Search
CPC .......................... G01M 11/31; G01M 11/3154
USPC ....................................................... 356/73.1
See application file for complete search history.

(56) References Cited

U.S. PATENT DOCUMENTS

| | | | | |
|---|---|---|---|---|
| 6,954,262 | B2 * | 10/2005 | Buzzetti ................. | G01M 11/33 356/237.1 |
| 2004/0001194 | A1 * | 1/2004 | Wilstrup .............. | G01M 11/333 356/73.1 |
| 2011/0085159 | A1 * | 4/2011 | Levin ..................... | G01M 11/30 356/73.1 |
| 2015/0092043 | A1 * | 4/2015 | Baribault ............. | H04N 5/2252 348/125 |
| 2015/0116700 | A1 * | 4/2015 | Meek ................... | G01M 11/331 356/73.1 |

FOREIGN PATENT DOCUMENTS

| | | |
|---|---|---|
| WO | WO-2012058641 A2 | 5/2012 |
| WO | WO-2013097041 A1 | 7/2013 |

OTHER PUBLICATIONS

Extended European Search Report for European Patent Application No. 14197815.5, dated Jun. 10, 2015.

(Continued)

*Primary Examiner* — Kara E Geisel
*Assistant Examiner* — Shawn Decenzo
(74) *Attorney, Agent, or Firm* — Locke Lord LLP; Scott D. Wofsy; Christopher J. Capelli

(57) ABSTRACT

An apparatus for fiber optic network testing includes a housing configured and adapted to couple to a mobile device and one or more network interfaces in communication with the housing. The one or more network interfaces are configured and adapted to operatively couple to a terminal end of a fiber optic cable. The apparatus also includes a magnification lens in operative communication with the housing and the one or more network interfaces.

13 Claims, 5 Drawing Sheets

(56) References Cited

OTHER PUBLICATIONS

Okada, M., Kihara, M., Hosoda, M., Toyonage, M.; "Simple Inspection Tool for Cleaved Optical Fiber Ends and Optical Fiber Connector End Surfaces;" International Wire & Cable Symposium, Proceedings of the 60th IWCS Conference, Technical Assistance and Support Center, NTT East Corporation, 1-2-5 Kamata-honcho, Ota-Ku, Tokyo 144-0053, Japan; pp. 270-274.

* cited by examiner

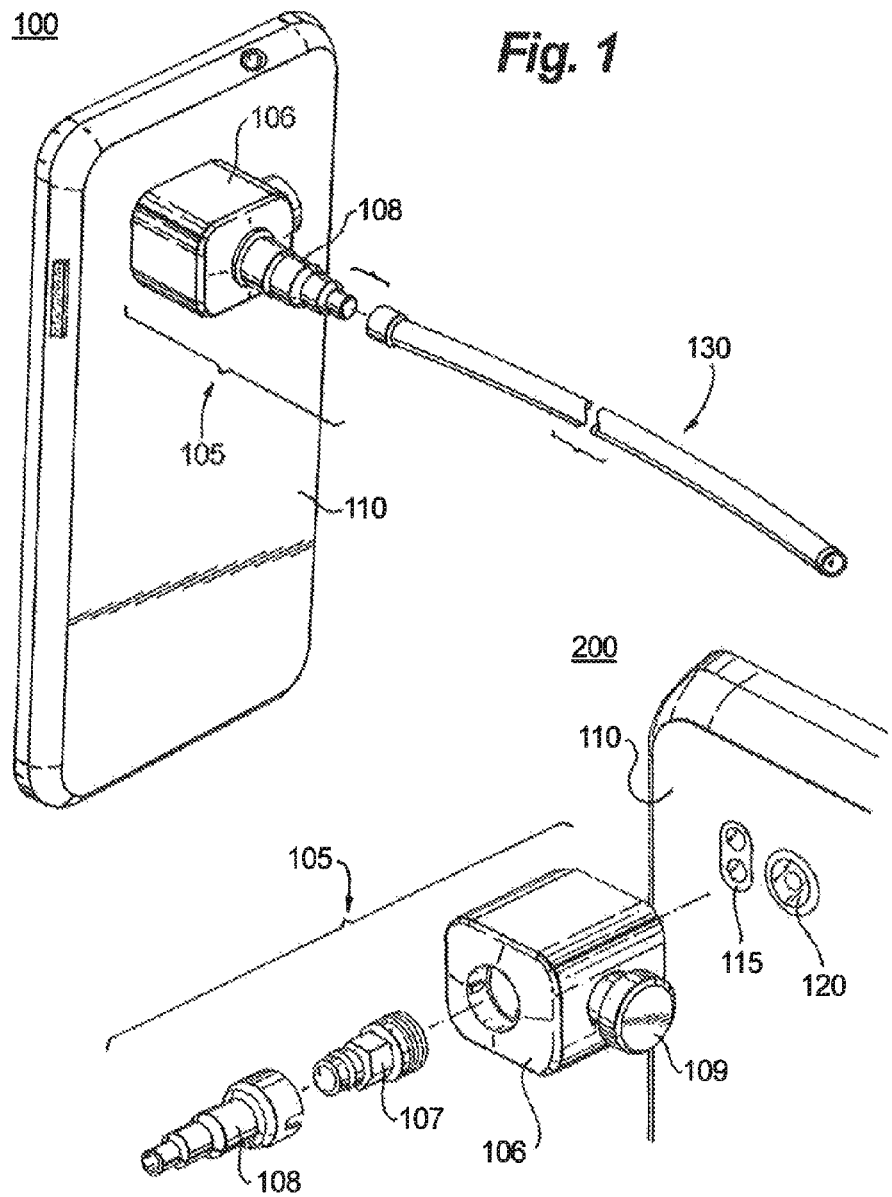

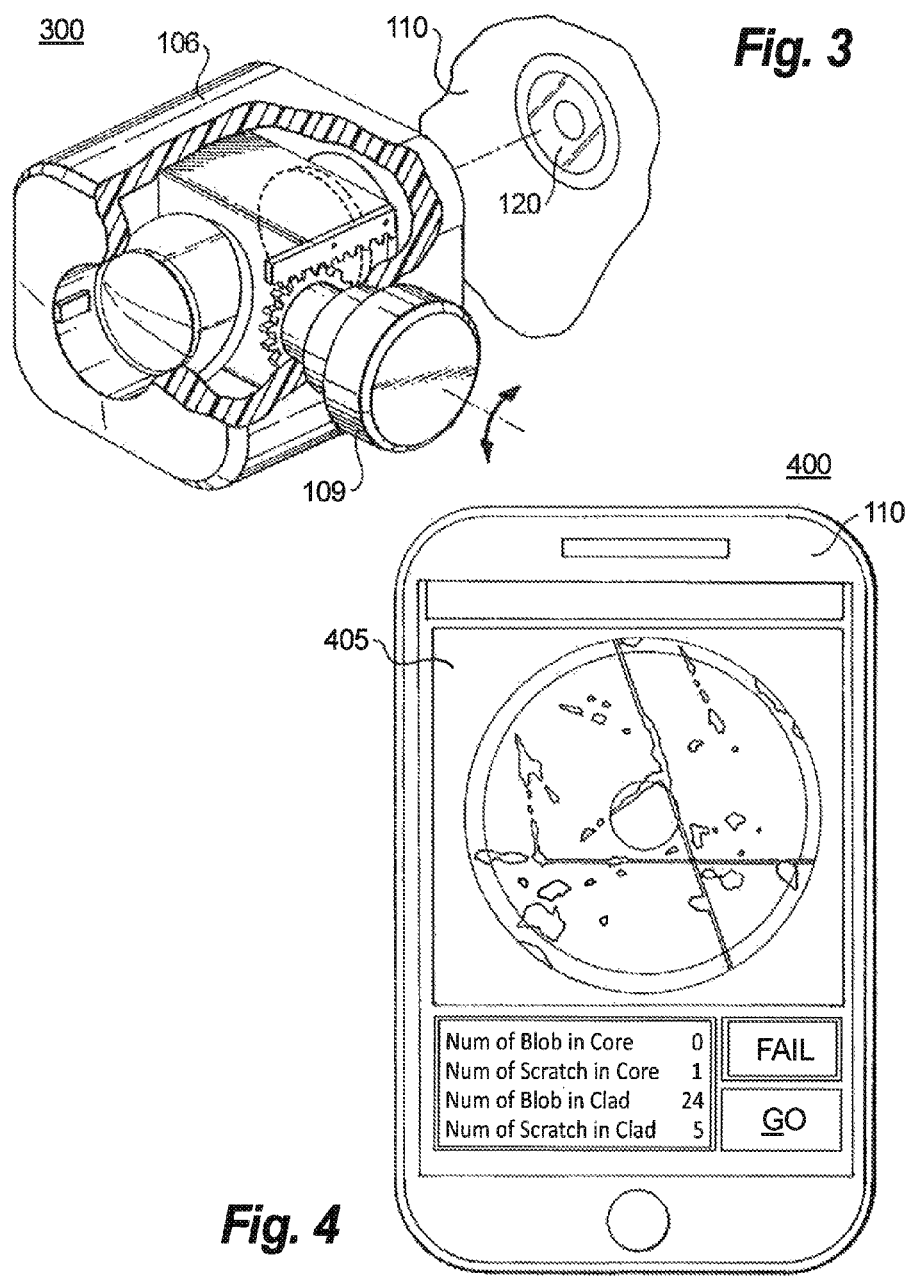

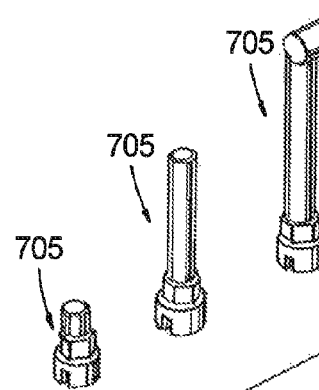
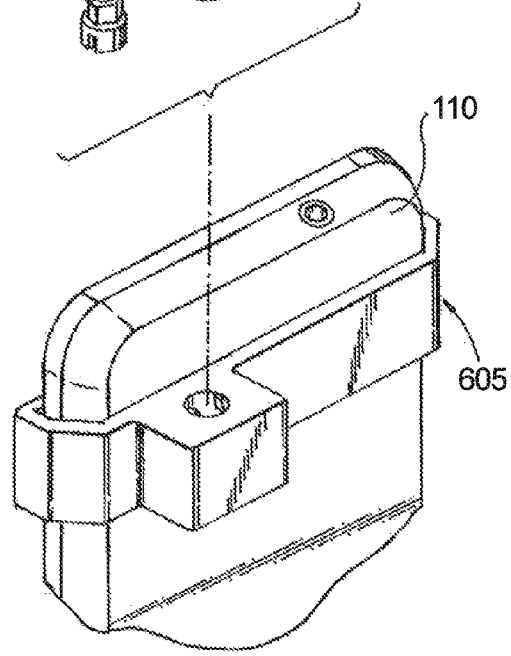
Fig. 7
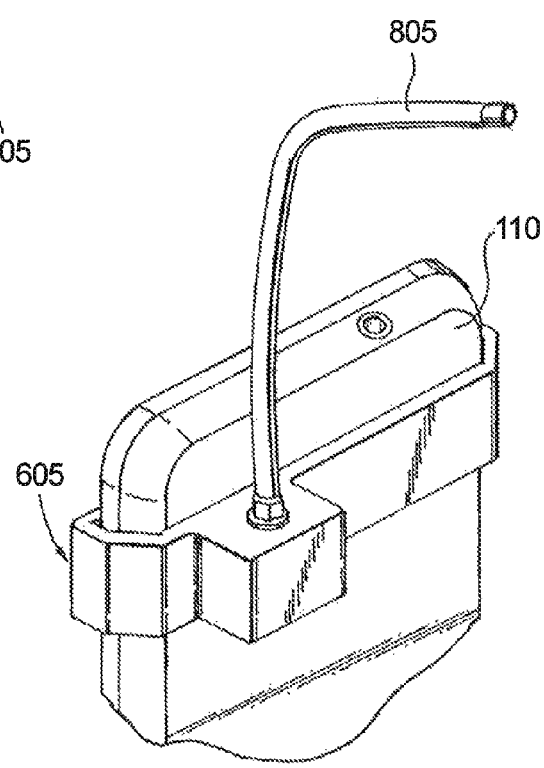
Fig. 8

SYSTEM AND APPARATUS FOR INSPECTING FIBER OPTIC CABLES

BACKGROUND

1. Field of the Invention

The present disclosure relates to network testing equipment, and more particularly to fiber optic network testing equipment.

2. Description of the Related Art

Fiber optic cable possesses numerous advantages over conventional coaxial electrical cable and other hardwired data transmission mediums. For example, because fiber optic cable carries no electricity, fiber optic systems are often more reliable and insensitive to cable damage than hardwire systems. In addition, fiber optic cable uses light for data transmission thereby supporting an increase in bandwidth.

Traditionally, testing fiber optic cables requires expensive and dedicated testing equipment (e.g., handheld network testers with a microscope and a digital camera, computers, etc.). Such dedicated testing equipment typically involves complex electronics, which directly corresponds to an increase in cost.

Although such conventional dedicated testing equipment has generally been considered satisfactory for its intended purpose, there is still a need in the art for simplified systems/devices for testing or inspecting fiber optic cables. There also remains a need in the art for such a fiber optic inspection systems/devices that are easy to make and use. The present invention provides a solution for these problems.

SUMMARY

Mobile devices such as smart phones, tablets and the like typically include high-resolution cameras and display screens (in addition to resident electronics such as processors, etc.). As described herein, the fiber optic test apparatus of the present disclosure converts such mobile devices into fiber optic testing devices. In particular, the fiber optic test apparatus includes a housing that is mounted to various models of mobile devices as well as a magnification lens, and a network interface (e.g., a terminal connector that mates with a fiber optic terminal connector). The apparatus is typically used in conjunction with an application resident on the mobile device, which displays an image of the fiber optic (e.g., taken by the mobile device's camera and light source). Operatively, the fiber optic test apparatus couples to a user's mobile device and assists the mobile device in image processing the fiber optic cable. Once an image is taken by the mobile device, it is analyzed the image of the fiber optic connector end-surface impurities or imperfections and displayed the image and the results (pass/fail) to a user.

According to one exemplary embodiment, the fiber optic test apparatus includes a housing configured and adapted to couple to a mobile device and one or more network interfaces in communication with the housing. The one or more network interfaces are configured and adapted to operatively couple to a terminal end of a fiber optic cable. The apparatus also includes a magnification lens in operative communication with the housing and the one or more network interfaces. In certain embodiments, the apparatus can further include a tuning knob in communication with the magnification lens, which adjusts a focal point of the magnification lens. Depending on the configuration of the to-be-tested fiber optic cable (e.g., located in a patch panel, hard to access installations, etc.), the apparatus further includes one or more extension cables configured to couple to the one or more network interfaces. The one or more network interfaces operatively receive the terminal end of the fiber optic cable via the extension cable(s).

Certain mobile devices also include a resident light source (e.g., an LED). According to another exemplary embodiment of this disclosure, the housing of the apparatus is configured and adapted to accommodate such resident light source of the mobile device thereby causing the resident light source to provide illumination to the fiber optic cable during testing procedures (e.g., when the camera is imaging the fiber optic cable). However, in other embodiments the apparatus includes a light source.

With respect to the housing of the fiber optic test apparatus, certain embodiments include an integrated case or molding (e.g., a mobile phone case, etc.) that couples to the mobile device. In other embodiments, the housing is configured and adapted to couple to the mobile device via two opposed rails that attach or clip to corresponding opposed sides of the mobile device.

These and other features of the systems and methods of the subject invention will become more readily apparent to those skilled in the art from the following detailed description of the preferred embodiments taken in conjunction with the drawings.

BRIEF DESCRIPTION OF THE DRAWINGS

So that those skilled in the art to which the subject invention appertains will readily understand how to make and use the devices and methods of the subject invention without undue experimentation, preferred embodiments thereof will be described in detail herein below with reference to certain figures, wherein:

FIG. 1 is a perspective view of an exemplary embodiment of a fiber optic inspection apparatus coupled to a mobile device constructed in accordance with the present invention;

FIG. 2 is an exploded perspective view of the fiber optic inspection apparatus illustrated in FIG. 1, showing a housing, a lens, and an optical terminal connector;

FIG. 3 is a partial cut-away perspective view of the housing showing an adjustment feature;

FIG. 4 is a display screen of the mobile device shown in FIG. 1, showing a status of a fiber optic cable;

FIG. 7 is a perspective view of the fiber optic inspection apparatus illustrated in FIG. 6, showing additional extension adapters; and FIG. 8 is a perspective view of the fiber optic inspection apparatus illustrated in FIG. 7, showing one of the extension adapter coupled to the fiber optic inspection apparatus;

A component or a feature that is common to more than one drawing is indicated with the same reference number in each of the drawings.

DESCRIPTION OF EXAMPLE EMBODIMENTS

Figure 5A:
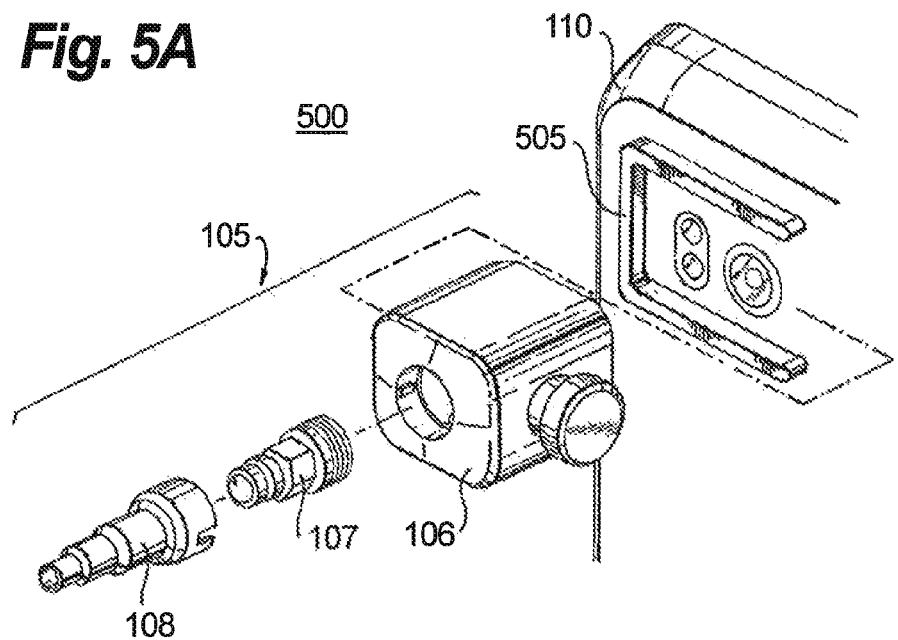
FIG. 5A is an exploded perspective view of the fiber optic inspection apparatus configured to couple to a mobile device according to another exemplary embodiment of this disclosure.

Reference will now be made to the drawings wherein like reference numerals identify similar structural features or aspects of the subject invention. For purposes of explanation and illustration, and not limitation, a partial view of an exemplary embodiment of the fiber optic cable inspection apparatus in accordance with the invention is shown in FIG. 1 and is designated generally by reference character 105. Other embodiments of the fiber optic cable inspection apparatus in accordance with this disclosure, or aspects thereof, are provided in FIGS. 2-8, as will be described. The fiber optic cable inspection apparatus can be used for example to inspect terminal ends of fiber optic cables using a mobile device (e.g., a mobile phone, a tablet, a laptop, a computer, and the like).

Still referring to FIG. 1, a perspective view 100 of fiber optic cable inspection apparatus 105 is shown. Perspective view 100 particularly illustrates fiber optic cable inspection apparatus 105 coupled to a mobile device 110 (shown as a mobile phone) via a housing 106. Although fiber optic cable inspection apparatus 105 is shown as coupled to mobile device 110, it is appreciated by this disclosure that housing 106 can readily be configured to couple to any number of devices such as, but not limited to laptops, tablets, computers, etc. As shown in FIG. 1, fiber optic cable inspection apparatus 105 receives or couples to a corresponding fiber optic cable 130. Further, fiber optic cable inspection apparatus 105 also includes a network interface 108 (e.g., a terminal adapter) configured and adapted to operatively receive (e.g., couple with) a terminal end of a fiber optic cable (not shown).

Referring now to FIG. 2, there is shown an exploded perspective view 200 of the fiber optic inspection apparatus 105. Exploded perspective view 200 illustrates various components of the fiber optic inspection apparatus 105, including housing 106, network interface 108 and an optical lens 107, which preferably is situated intermediate to housing 106 and network interface 108. Optical lens 107 is preferably a microscope lens that operatively provides magnified views of a fiber optic cable when lens is coupled or attached to network interface 108, as discussed below. Further, housing 106 also preferably includes an adjustment knob 109 that changes a focal length of optical lens 107.

For example, referring to FIG. 3, a partial cut-away view 300 of housing 106 showing the operation of an adjustment feature (i.e., knob 109), which functions to move or adjust optical lens 107.

As discussed above, and referring collectively to FIGS. 1-3, fiber optic inspection apparatus 105 couples or attaches to mobile device 110. Fiber optic inspection apparatus 105, as shown in FIG. 2, preferably couples to a resident light source (e.g., Light Emitting Diode (LED) 115) and resident camera 120 on mobile device 110. Typically, a user of mobile device 110, uses a locally running application (that uses, for example, camera 120 and/or LED 115) and analyzes images from optic inspection apparatus 105 to determine a state of the attached fiber optic cable. Notably, in alternative embodiments, the light source maybe independently provided (e.g., not resident on mobile device 110). For example, the light source can be incorporated within housing 106.

FIG. 4 provides a display screen 405 of the mobile device 110, showing a status of a fiber optic cable attached to fiber optic inspection apparatus 105 (not shown). As illustrated, a status of the fiber optic cable can include a number of blobs and scratches in a core or a clad. The user analyzes the status of the fiber optic cable and indicates or selects "FAIL" or "GO" (e.g., pass, etc.). Once selected, the application running on mobile device 110 can save the selection, transmit the data to one or more additional users, devices, etc., and/or take subsequent corrective action (if necessary).

Figure 5B:
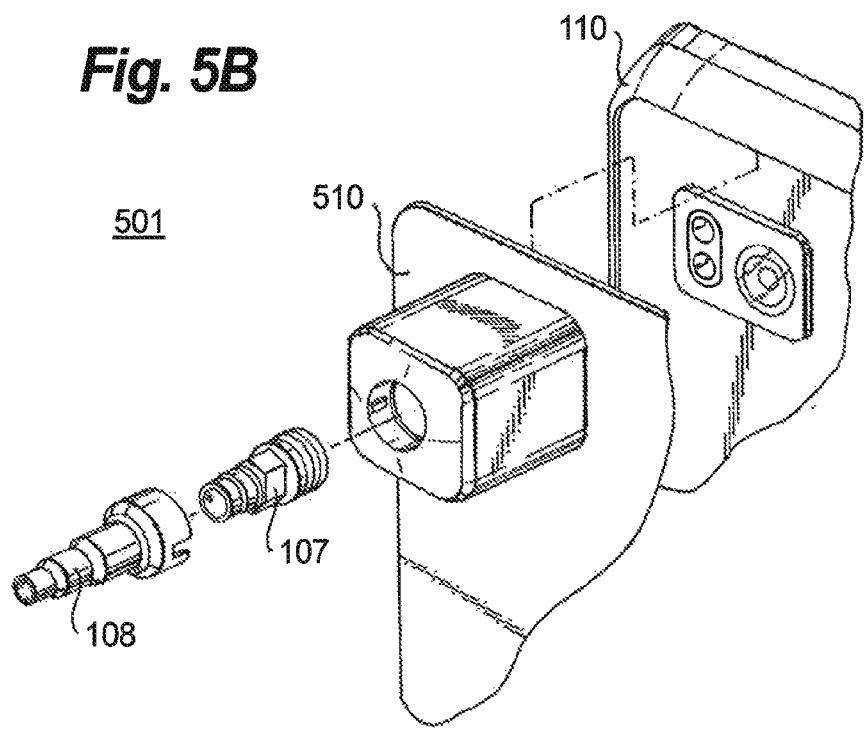
FIG. 5B is an exploded perspective view of the fiber optic inspection apparatus configured as a mobile phone case that couples a mobile device according to another exemplary embodiment of this disclosure.

FIGS. 5A-5B illustrate two other embodiments of the fiber optic inspection apparatus. In particular, FIG. 5A provides an exploded perspective view 500 of the fiber optic inspection apparatus configured to couple to mobile device 110 via molding 505. Molding 505 can be integrated into mobile device 110 by, for example, incorporating molding during manufacture of mobile device 110 or adding molding post manufacture via an adhesive, etc., and the like. Operatively, fiber optic inspection apparatus 105 couples molding 505 thereby attaching to mobile device 110.

FIG. 5B illustrates an exploded perspective view of the fiber optic inspection apparatus configured as a mobile phone case 510 that couples mobile device 110. As shown, housing 106 is formed integral with mobile phone case 510. However, in other embodiments, it is appreciated that mobile phone case 510 and housing 106 can be coupled by other known means (e.g., a snap closure, adhesive, etc.).

Figure 6:
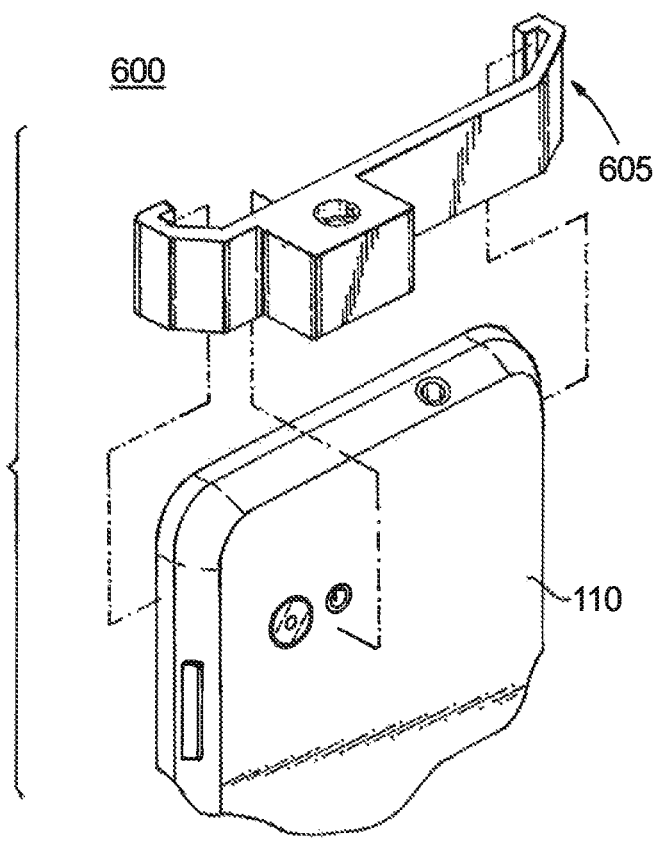
FIG. 6 is a perspective view of a fiber optic inspection apparatus coupled to the mobile device according to another exemplary embodiment of the disclosure.

FIGS. 6-8 are perspective views of a fiber optic inspection apparatus 605 configured as a clip on adapter that couples to mobile device 110. Referring now to FIG. 6, fiber optic inspection apparatus 605 includes a pair of opposed rails or arms that clip to corresponding opposed sides of mobile device 110. Notably, as shown, the fiber optic inspection apparatus 605 operatively couples to the resident camera and light source (e.g., an LED) of mobile device 110.

FIG. 7 shows the fiber optic inspection apparatus 605 attached to mobile device 110 as well as additional extension adapters 705 that can be interchangeable used in conjunction with clip 605. For example, the extension adapters can fit various types of fiber optic terminal ends and/or be of varying lengths depending on a location of the fiber optic terminal.

FIG. 8 is a perspective view of the fiber optic inspection apparatus illustrated in FIG. 7, showing an extension adapter 805 coupled to fiber optic inspection apparatus 605. As shown, extension can have a threaded design that mates with a corresponding threading of fiber optic inspection apparatus 605.

The techniques described herein, therefore, provide for an improved network test apparatus that adapts a mobile device for network testing purposes (e.g., testing fiber optic cables or wires). In particular, the techniques herein provide a low cost and easy to manufacture apparatus that leverages resident electronics (e.g., processors, displays, cameras, light sources, etc.) of mobile devices. In this fashion, a network tester does not need to bring dedicated testing equipment that can be both burdensome to travel with as well as expensive to maintain.

While there have been shown and described illustrative embodiments that provide for a network testing apparatus that couples to a mobile device, it is to be understood that various other adaptations and modifications may be made within the spirit and scope of the embodiments herein. For example, the embodiments have been shown and described herein with relation to a mobile device 110, shown as a mobile phone. However, the embodiments in their broader sense are not as limited, and may, in fact, be used with other types of mobile phones, tablets, and various other electronics.

The foregoing description has been directed to specific embodiments. It will be apparent, however, that other variations and modifications may be made to the described embodiments, with the attainment of some or all of their advantages. Accordingly this description is to be taken only by way of example and not to otherwise limit the scope of the embodiments herein. Therefore, it is the object of the appended claims to cover all such variations and modifications as come within the true spirit and scope of the embodiments herein.

What is claimed is:

1. An apparatus for fiber optic network testing, comprising:
a housing configured and adapted to couple to a mobile device;
one or more network interfaces in communication with the housing, the one or more network interfaces configured and adapted to operatively couple to a fiber optic cable under test;
a magnification lens in operative communication with the housing and the one or more network interfaces;
an extension cable configured to couple to the one or more network interfaces, wherein the one or more network interfaces operatively receive an image of the fiber optic cable under test via the extension cable; and
an application hosted at least partially on the mobile device, the application configured to:
display on the mobile device the fiber optic cable under test, the fiber optic cable under test having a core and a clad;
display on the mobile device a state of the fiber optic cable, the state of the fiber optic cable includes each of the following: a number of blobs in the core of the fiber optic cable, a number of scratches in the core of the fiber optic cable, a number of blobs in the clad of the fiber optic cable, and a number of scratches in the clad of the fiber optic cable;
display on the mobile device indicia to be selected by the user indicating a fail status and pass status for the coupled fiber optic cable; and
selectively take a corrective action based on the indicia selected by the user regarding the state of the fiber optic cable.

2. The apparatus of claim 1, further comprising:
a tuning knob, in communication with the magnification lens, that adjusts a focal point of the magnification lens.

3. The apparatus of claim 1, wherein the housing is further configured and adapted to accommodate a resident light source of the mobile device thereby causing the resident light source to provide illumination to the fiber optic cable under test during testing procedures.

4. The apparatus of claim 3, wherein the housing is further configured to substantially surround a backside of the mobile device.

5. The apparatus of claim 1, further comprising:
a light source configured to communicate with the housing, the light source illuminating the fiber optic cable under test.

6. The apparatus of claim 5, wherein the light source is operatively coupled to the housing.

7. The apparatus of claim 1, wherein the one or more network interfaces, when operatively coupled to a terminal end of the fiber optic cable under test causes the application to display the fiber optic cable and provide the image on a display of the mobile device.

8. The apparatus of claim 1, wherein the housing is configured and adapted to couple to the mobile device via two opposed rails that attach to corresponding opposed lateral sides of the mobile device.

9. An apparatus for fiber optic network testing, comprising:
a housing configured and adapted to couple to a mobile device;
one or more network interfaces in communication with the housing, the one or more network interfaces configured and adapted to operatively couple to a fiber optic cable under test;
a magnification lens in operative communication with the housing and the one or more network interfaces;
a camera that images the fiber optic cable under test and operatively coupled to the magnification lens, the housing and the one or more network interfaces;
an extension cable configured to couple to the one or more network interfaces, wherein the one or more network interfaces operatively receive the image of the fiber optic cable under test via the extension cable;
a light source that illuminates the fiber optic cable under test when the camera is imaging; and
an application hosted at least partially on the mobile device, the application configured to:
display on the mobile device the fiber optic cable under test, the fiber optic cable under test having a core and a clad;
display on the mobile device a state of the fiber optic cable, the state of the fiber optic cable includes each of the following: a number of blobs in the core of the fiber optic cable, a number of scratches in the core of the fiber optic cable, a number of blobs in the clad of the fiber optic cable, and a number of scratches in the clad of the fiber optic cable;
display on the mobile device indicia to be selected by the user indicating a fail status and pass status for the coupled fiber optic cable; and
selectively take a corrective action based on the indicia selected by the user regarding the state of the fiber optic cable.

10. The apparatus of claim 9, further comprising:
a tuning knob, in communication with the magnification lens, that adjusts a focal point of the magnification lens.

11. The apparatus of claim 9, wherein the housing is further configured to substantially surround a backside of the mobile device.

12. The apparatus of claim 9, wherein the one or more network interfaces, when operatively coupled to a terminal end of the fiber optic cable under test causes the application to display the fiber optic cable and provide the image on a display of the mobile device.

13. The apparatus of claim 9, wherein the housing is configured and adapted to couple to the mobile device via two opposed rails that attach to corresponding opposed lateral sides of the mobile device.

* * * * *